(12) United States Patent
Fuimaono et al.

(10) Patent No.: US 9,078,567 B2
(45) Date of Patent: Jul. 14, 2015

(54) METHOD AND DEVICE FOR VISUALLY SUPPORTING AN ELECTROPHYSIOLOGY CATHETER APPLICATION IN THE HEART

(75) Inventors: Kristine Fuimaono, West Berlin, NJ (US); Gal Hayam, Tivon (IL); Yuval Karmi, Hadera (IL); Reinmar Killmann, Forchheim (DE); Assaf Preiss, Bet Yizhaq (IL); Norbert Rahn, Forchheim (DE); Frank Sauer, Princeton, NJ (US); Chenyang Xu, Allentown, NJ (US)

(73) Assignees: SIEMENS AKTIENGESELLSCHAFT, Munich (DE); BIOSENSE WEBSTER, Diamond Bar, CA (US)

( * ) Notice: Subject to any disclaimer, the term of this patent is extended or adjusted under 35 U.S.C. 154(b) by 2068 days.

(21) Appl. No.: 10/569,958

(22) PCT Filed: Aug. 19, 2004

(86) PCT No.: PCT/EP2004/009314
§ 371 (c)(1),
(2), (4) Date: Nov. 3, 2006

(87) PCT Pub. No.: WO2005/027765
PCT Pub. Date: Mar. 31, 2005

(65) Prior Publication Data
US 2007/0078325 A1    Apr. 5, 2007

(30) Foreign Application Priority Data
Sep. 1, 2003   (DE) .................................. 103 40 544

(51) Int. Cl.
*A61B 5/05* (2006.01)
*A61B 6/03* (2006.01)
(Continued)

(52) U.S. Cl.
CPC ............... *A61B 6/032* (2013.01); *A61B 5/055* (2013.01); *A61B 8/14* (2013.01); *A61B 5/7285* (2013.01);
(Continued)

(58) Field of Classification Search
CPC ...................................................... A61B 6/541
USPC ........................................................... 600/407
See application file for complete search history.

(56) References Cited

U.S. PATENT DOCUMENTS 5,526,812 A   6/1996  Dumoulin et al.
5,846,198 A  12/1998  Killmann
(Continued)

FOREIGN PATENT DOCUMENTS

EP   0 945 104 A    9/1999
EP   0 945 104 A1   9/1999
(Continued)

OTHER PUBLICATIONS

Van Der Velde et al., "Fusion of Electrophysiology Mapping Data and Angiographic Images to Facilitate Radiofrequency Ablation", Computers in Cardiology, 2000, pp. 85-87.
(Continued)

*Primary Examiner* — Tse Chen
*Assistant Examiner* — Hien Nguyen
(74) *Attorney, Agent, or Firm* — Harness, Dickey & Pierce, P.L.C.

(57) ABSTRACT

The invention relates to a method and a device for visually supporting an electrophysiology catheter application in the heart, whereby electroanatomical 3D mapping data of an area of the heart to be treated which are provided during performance of the catheter application are visualized. Before the catheter application is carried out, 3D image data of the area to be treated are recorded by means of a tomographical 3D imaging method, a 3D surface profile of objects in the area to be treated is extracted from the 3D image data by segmentation and the electroanatomical 3D mapping data provided and the 3D images representing the 3D surface profile are associated with each other in the correct position and dimension relative each other and e.g. visualized in an superimposed manner during the catheter application. The present method and the corresponding device allow for an improved orientation of the user who carries out an electrophysiology catheter application in the heart.

14 Claims, 1 Drawing Sheet

(51) Int. Cl.
   *A61B 5/055*   (2006.01)
   *A61B 8/14*    (2006.01)
   *A61B 5/00*    (2006.01)
   *A61B 6/00*    (2006.01)
   *A61B 8/00*    (2006.01)
   *A61B 18/14*   (2006.01)
   *A61B 18/00*   (2006.01)
   *G01R 33/56*   (2006.01)

(52) U.S. Cl.
   CPC .............. *A61B 6/5247* (2013.01); *A61B 6/541* (2013.01); *A61B 8/543* (2013.01); *A61B 18/1492* (2013.01); *A61B 2018/00375* (2013.01); *A61B 2018/00839* (2013.01); *G01R 33/5608* (2013.01)

(56) References Cited

U.S. PATENT DOCUMENTS

| | | | |
|---|---|---|---|
| 6,058,218 | A | 5/2000 | Cline |
| 6,556,695 | B1 * | 4/2003 | Packer et al. ............... 382/128 |
| 6,572,476 | B2 * | 6/2003 | Shoji et al. ................... 463/33 |
| 6,711,433 | B1 | 3/2004 | Geiger et al. |
| 6,865,248 | B1 | 3/2005 | Rasche et al. |
| 2001/0036303 | A1 * | 11/2001 | Maurincomme et al. ...... 382/132 |
| 2002/0065456 | A1 * | 5/2002 | Bazin et al. ................. 600/407 |
| 2002/0087329 | A1 * | 7/2002 | Massaro et al. .............. 704/275 |
| 2002/0176608 | A1 * | 11/2002 | Rose .......................... 382/108 |
| 2003/0018251 | A1 * | 1/2003 | Solomon ..................... 600/427 |
| 2003/0153907 | A1 | 8/2003 | Panescu et al. |
| 2003/0187358 | A1 | 10/2003 | Okerlund et al. |
| 2004/0029068 | A1 * | 2/2004 | Sachdeva et al. ............. 433/24 |
| 2004/0233217 | A1 * | 11/2004 | Chiu et al. .................... 345/601 |
| 2007/0055142 | A1 * | 3/2007 | Webler ......................... 600/425 |

FOREIGN PATENT DOCUMENTS

| | | | |
|---|---|---|---|
| EP | 0945104 | A1 | 9/1999 |
| JP | 9006986 | A | 1/1997 |
| JP | 2000-279425 | | 10/2000 |
| JP | 2000279425 | A | 10/2000 |
| JP | 2001-070269 | | 3/2001 |
| JP | 2001-340336 | | 12/2001 |
| JP | 2001340336 | A | 12/2001 |
| JP | 2002-345725 | | 12/2002 |
| JP | 2002345725 | A | 12/2002 |
| JP | 2003517361 | T | 5/2003 |
| WO | WO 00/25672 | | 5/2000 |
| WO | WO 00/25672 | A | 5/2000 |
| WO | WO 02/062265 | A2 | 8/2002 |
| WO | WO 02/100285 | | 12/2002 |
| WO | WO 02100285 | A1 | 12/2002 |

OTHER PUBLICATIONS

Paul F. Hemler et al.: << A System for Multimodality Image Fusion >>, Seventh Annual IEEE Symposium on Computer-Based Medical Systems, 1994, SA5: Image Processing 4, pp. 335-340.

Et van der Velde et al.: "Fusion of Electrophysiology Mapping Data and Angiographic Images to Facilitate Readiofrequency Ablation", in: Computers in Cardiology, vol. 27, 2000, pp. 85-87.

S.Kewitz et al.: "A New Method of Cardiac Activation Mapping: an Experimental Study", in: Computers in Cardiology, vol. 27, 2000, pp. 509-512.

Dorin Panescu et al.: "Electro-anatomical Four-dimensional Mapping of Ventricular Tachycardia", Proceedings of the 23$^{rd}$ Annual EMBS International Conference, Oct. 25-28, 2001, Turkey, pp. 405-407.

International Search Report and German Office Action.

Office Action for corresponding Japanese Application No. 2006-525065 dated Apr. 30, 2009 with English translation.

Office Action dated Mar. 2, 2010 in corresponding Japanese Patent Application No. 2006-525065 and English Translation thereof.

K. Watabe, "Multi-modality Image Positioning and Superposition", Japanese Society of Radiological Technology, Academic Journals, Jan. 2003, vol. 59, No. 1, 60-65, and English translation thereof.

* cited by examiner

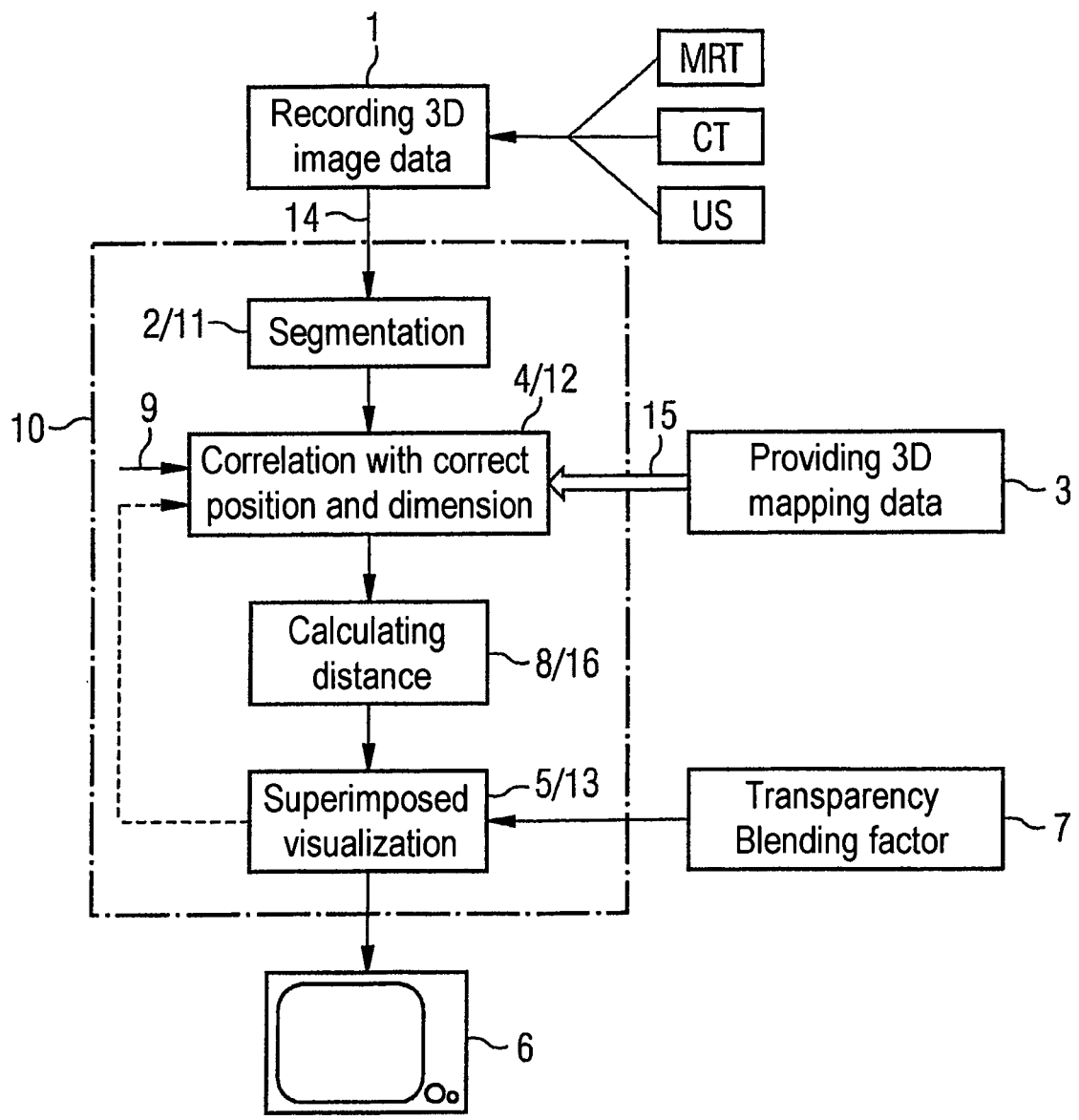

METHOD AND DEVICE FOR VISUALLY SUPPORTING AN ELECTROPHYSIOLOGY CATHETER APPLICATION IN THE HEART

This application is the national phase under 35 U.S.C. §371 of PCT International Application No. PCT/EP2004/009314 which has an International filing date of Aug. 19, 2004, which designated the United States of America and which claims priority on German Patent Application number 103 40 544.5 filed Sep. 1, 2003, the entire contents of which are hereby incorporated herein by reference.

FIELD

The present invention generally relates to a method and/or to a device for visually supporting an electrophysiology catheter application in the heart. For example, it may relate to one whereby electroanatomical 3D mapping data of an area of the heart to be treated, which are provided during the performance of catheter application, are visualized.

BACKGROUND

The treatment of cardiac arrhythmia has changed considerably since the introduction of the technology of catheter ablation by way of high-frequency current. In this technology, an ablation catheter is introduced into one of the heart chambers via veins or arteries under X-ray control and the tissue causing the cardiac arrhythmia is removed by high-frequency current.

The prerequisite for performing a catheter ablation successfully is that the cause of the cardiac arrhythmia is accurately located in the heart chamber. This locating is done via an electrophysiological investigation during which electrical potentials are detected spatially resolved with a mapping catheter introduced into the heart chamber. This electrophysiological investigation, the so-called electroanatomical mapping, thus provides 3D mapping data which can be displayed on a monitor. In many cases, the mapping function and the ablation function are combined in one catheter so that the mapping catheter is also an ablation catheter at the same time.

A known electroanatomical 3D mapping method such as can be performed by way of the carto system by the company Biosense Webster Inc., USA, is based on electromagnetic principles. Underneath the examining table, three different low-intensity alternating magnetic fields are built up. Using integrated electromagnetic sensors at the catheter point of the mapping catheter, it is possible to measure the voltage changes induced by catheter movements within the magnetic field and to calculate the position of the mapping catheter at any time with the aid of mathematical algorithms. Probing the endocardial contour of a heart chamber point by point with the mapping catheter and simultaneously detecting the electrical signals produces an electroanatomical three-dimensional map in which the electrical signals are reproduced color coded.

As a rule, the orientation of the operator required for guiding the catheter has hitherto been effected via fluoroscopic visualization. Since, in electroanatomical mapping, the position of the mapping catheter is known at any time with this technology, the orientation can also take place by continuous representation of the catheter point in the electroanatomical map after a sufficiently large number of measuring points has been detected, so that fluoroscopic imaging technology with X-ray screening can be omitted at this stage.

A fundamental problem in performing the catheter ablation inside the heart is that it has hitherto not been possible to provide optimal orientation of the operator during the guidance of the catheter. A more accurate representation of the morphological environment during the guidance of the catheter which, on the one hand, increase the accuracy during the catheter ablation and, on the other hand, of shortening the time for performing the electroanatomical mapping. Furthermore, the X-ray screening still required for the electroanatomical mapping in many cases could be reduced or avoided in that the X-ray dose applied could also be reduced.

To improve the orientation of the operator when guiding the catheter, different techniques are known. In one technique, a special catheter with an ultrasonic probe is used as is offered, for example, by company Siemens AG Medical Solutions under the title Acunav. Parts of the target tissue to be removed, together with the catheter, can be visualized in real-time via a two-dimensional ultrasonic detection of the environment and of a part of the catheter. However, using such a catheter does not supply three-dimensional image information. The ultrasonic representation can only be used, therefore, in order to insert, for example, a so-called loop catheter into the opening of a pulmonary vein. After the loop catheter has been positioned, tissue removal around the opening of the pulmonary vein can be performed by visualizing both the loop catheter and the ablation catheter by way of X-radiation.

In another known technique, a loop catheter is placed at the opening of the pulmonary vein without the support of imaging 2D ultrasonic technology by applying a contrast medium via a catheter placed in the left atrium in the area of the pulmonary vein opening under X-ray screening. During this process, the contrast medium becomes distributed and a small proportion leaves with the blood flow via the pulmonary vein. This short-time visualization of the pulmonary vein enables the loop catheter to be placed in the opening. The catheter ablation can then be performed as with the above-mentioned technique.

A technique is also known in which the opening of the pulmonary vein is located by electroanatomical mapping of the left atrium and of the pulmonary veins by first introducing the mapping catheter into the pulmonary vein and then pulling it back until electrical activity of the atrium is detected. This position corresponds to the position of the opening of the pulmonary vein around which the target tissue is to be removed.

SUMMARY

It is an object of at least one embodiment of the present invention to specify a method and a device for visually supporting an electrophysiology catheter application in the heart which provides for, for example, improved orientation during the guidance of the catheter during the catheter application, particularly in electroanatomical mapping and/or during a catheter ablation.

In the present method of at least one embodiment, for visually supporting an electrophysiology catheter application in the heart, particularly a catheter ablation, 3D image data of the area to be treated are first recorded by way of a tomographical 3D imaging method before the catheter application is carried out. From the 3D image data, a 3D surface profile of objects, particularly one or more heart chambers or vessels, in the area to be treated is extracted by segmentation. The 3D image data representing the 3D surface profile, called selected 3D image data in the text that follows, are associated with the electroanatomical 3D mapping data provided during the performance of the catheter application in the correct position and dimension. The 3D mapping data and at least the selected 3D image data are then visualized superimposed on one another in the correct position and dimension in a visual representation during the performance of the catheter application.

Due to this superposition of the 3D surface profile, by which the morphology of the area to be treated or being treated is reproduced in good quality, with the electroanatomical 3D mapping data recorded during the performance of the catheter application, a better orientation and more accurate details are conveyed to the operator of the catheter during the performance of the catheter application than is the case in the previously known methods for visual support. The superimposed imaging can take place, for example, on a monitor in the control room or in the operating room itself. On the monitor, the operator then recognizes the anatomical tissue and its electrophysiological characteristics in a real-time display during the performance of the catheter application. This provides for a safe and accurate way of working.

For recording the 3D image data, methods of X-ray computer tomography, of magnetic resonance tomography or of 3D ultrasonic imaging can be used, for example. Combinations of these imaging methods are also possible, of course. It is only necessary to pay attention to the fact that the 3D image recordings take place in the same heart phase as the electroanatomical 3D mapping data provided so that in each case the same state of the heart is observed. This can be ensured with the familiar technology of ECG gating during the recording of the image data and of the electroanatomical mapping data.

Different techniques can be used for segmenting the 3D image data recorded. Thus, the three-dimensional surface profile of the objects contained in the 3D image data, particularly of the vessels and/or one or more heart chambers, can be produced, for example, by segmenting all 2D layers obtained with the imaging method. Apart from this layered segmentation, a 3D segmentation of one or more chambers and/or vessels is also possible. Suitable segmentation techniques are known to the expert in the field of image processing of medical image data.

Correlating the electroanatomical 3D mapping data with the selected 3D image data in the correct dimension and position can be done by way of different techniques. One possibility resides in registration between the respective data by visually matching the 3D surface profile with the representation of the electroanatomical 3D mapping data. Furthermore, artificial markers or natural distinct points can be used which can be recognized in both records. Apart from the area to be treated, a neighboring area can also be used for the registration if it is contained in the existing data. Furthermore, it is possible to place the center on data in the environment of the tissue to be removed, also called the target tissue in the text which follows, or of the catheter point during the performance of the registration.

In an advantageous embodiment of the method and of the device, the registration takes place in a first stage in which only a relatively small portion of the electroanatomical 3D mapping data is present, with the aid of artificial markers or of distinct points, and in one or more subsequent stages in which a greater number of electroanatomical 3D mapping data is already present, by surface matching. In this manner, the registration is improved with the increasing number of electroanatomical 3D mapping data during the catheter application.

During the superimposition of the electroanatomical 3D mapping data on the 3D image data, these 3D image data can be represented by way of a volume rendering technique. In a further embodiment, the 3D surface profile is represented by a polygonal grid as is known from the field of computer graphics. The superimposition can be performed with adjustable transparency and adjustable blending factor. It is also possible to calculate and display an endoscopic perspective. Since the electroanatomical 3D mapping data also contains the respective instantaneous position of the catheter point, it is also possible to visualize only the position of the catheter in real-time in the representation of the 3D image data from time to time without displaying the remaining 3D mapping data.

Furthermore, the distance of the catheter to any picture elements of the 3D image data can be calculated due to the registration between the 3D mapping data and the 3D image data. This is made possible by an advantageous embodiment of the present method in which the catheter point is displayed colored in the visualization, the color changing in dependence on the distance from predeterminable picture elements, particularly the position of the target tissue.

The present device of at least one embodiment for performing the method of at least one embodiment includes one or more input interfaces for the electroanatomical 3D mapping data and the 3D image data recorded by means of an imaging tomographic method. The device exhibits a segmentation module for segmenting the 3D image data in order to extract a 3D surface profile of objects contained inside the volume recorded by way of the 3D image data. This segmentation module is connected to a registration module which is constructed for correlation with the correct position and dimension of the electroanatomical 3D mapping data and the 3D image data, representing the 3D surface profile. This registration module, in turn, is connected to a visualization module which superimposes the 3D mapping data and at least the 3D image data representing the 3D surface profile on one another in the correct position with the correct dimension, for visualization by way of a display device, particularly a monitor or projector.

The individual modules of the device are constructed in different embodiments corresponding to the performance of the different embodiments of the method described in the text which follows.

BRIEF DESCRIPTION OF THE DRAWINGS

In the text which follows, embodiments of the present method and associated device will again be explained in greater detail in connection with the FIGURE.

For this purpose, the FIGURE shows the individual steps in the performance of the present method and individual modules of the associated device, respectively.

DETAILED DESCRIPTION OF THE EXAMPLE EMBODIMENTS

In a first step 1 in the present method, the 3D image data of the area to be treated, particularly of the heart chamber to be treated, are recorded. During the recording of these 3D image data, a larger part of the heart can also be included for the registration to be performed later. The 3D image data are recorded by way of a method of tomographic 3D imaging such as, for example, X-ray computer tomography, magnetic resonance tomography or 3D ultrasonic techniques. During the recording of the 3D image data, care must be taken that these image data are in each case recorded for the same heart phase for which the electroanatomical 3D mapping data will also be provided later. This is ensured by ECG gating of the image recording and recording of the 3D mapping data, for example by referring to a percentage of the RR interval or to a fixed time interval before or after the R peak.

During the performance of the method, it is of importance to record high-resolution image data of the heart chamber which is electroanatomically measured during the catheter application. Preferably, a contrast medium in association with a test bolus or bolus tracking is therefore used for recording the 3D image data.

In the second step, the segmentation 2 of the 3D image data for extracting the 3D surface profile of vessels and heart chambers contained therein takes place. This segmentation is required, on the one hand, for the later representation of the surface profile of these objects in the superimposed image representation and, on the other hand, in an advantageous embodiment of the method, for the correlation with the 3D mapping data in the correct position and dimension.

The segmentation takes place in the segmentation module 11 of the present device 10. This segmentation module 11 receives the recorded 3D image data via a corresponding input interface 14. In the same way, the 3D mapping data are supplied to the device 10 via the same or another interface 15, as a rule continuously, during the period of the electrophysiological catheter application.

As a rule, electrophysiological procedures are only performed in one of the heart chambers. By heart chambers, both the ventricle and the atria are meant in the text which follows. In addition to this chamber to be treated, it is also possible to measure other chambers or vessels electroanatomically, for example the right atrium and the vena cava for a catheter ablation on the pulmonary vein in the left atrium. In this case, the electroanatomical 3D mapping data include one or more heart chambers and/or heart vessels.

The segmentation of the 3D image data can be applied in the same manner to one or more heart chambers and/or heart vessels such as, for example, the vena cava or the pulmonary veins in order to obtain all surfaces which are represented by the electroanatomical 3D mapping data. However, a registration by surface matching does not require segmentation of the entire surface or of the heart chamber to be treated, respectively. For this, it is sufficient to obtain a representation of the surface of an area of the chamber of interest, for example the left atrium, or of areas of heart vessels of interest, for example the pulmonary veins, by a few surface points by which the surface matching can be performed for the registration. On the other hand, however, it may be of advantage to include a larger area, particularly further heart chambers or vessels for the registration.

The segmentation of the heart chamber to be treated—or other chambers or heart vessels—can take place in the form of a 2D segmentation in individual layers. One possibility resides in performing a fully automatic segmentation of all layers of the heart chamber obtained by the imaging method. As an alternative, one or more of the layers can also be segmented interactively by an operator and the layers following in each case can be segmented automatically on the basis of the prior knowledge of the layers already segmented. The interactive segmentation of individual layers can also be supported by semiautomatic techniques such as, for example the technique of active contours. After the segmentation of all individual layers, the 3D surface profile of the heart chamber can then be reconstructed.

The segmentation can also take place as 3D segmentation of the heart chamber to be treated—or of other chambers or heart vessels—by way of known 3D segmentation techniques. Examples of such 3D segmentation techniques are the threshold technique or the technique of region growing. If these fully automatic 3D segmentation algorithms do not work reliably in individual cases, an interactive input capability for an operator can be provided in order to be able to specify, for example, gray scale thresholds or spatial blockers.

The 3D surface profile of the objects, obtained from the segmentation, is supplied to the registration module 12 in which the 3D image data or, respectively, the data of the 3D surface profile obtained from these, are correlated with the 3D mapping data provided in step 3 in the correct position and dimension. The 3D mapping data are obtained via a mapping catheter which supplies 3D coordinates of surface points of the heart chamber to be treated via a 6D position sensor integrated into the tip of the catheter. Such catheters are known from the prior art for catheter ablation or, respectively, electro-anatomical mapping.

In this process, the catheter is introduced into the respective heart chamber via veins or arteries by the operator. The guidance of the catheter and the recording of the 3D mapping data is not a component part of the present method. During the catheter ablation or the electroanatomical measuring of the heart chamber to be treated, respectively, increasingly more surface points are added to the mapping data in the course of time. These surface points are used for reconstructing the morphological structure of the chamber, i.e. for visualizing it. In this manner, an increasingly more detailed image of the heart chamber to be treated is produced from the electroanatomical 3D mapping data in the course of time.

In this context, it is also possible to record electro-anatomically and to reconstruct complete anatomical surfaces of other chambers, for example of the right atrium with the vena cava in the case of a catheter ablation at the opening of the pulmonary veins, before performing the catheter ablation. These electroanatomical 3D measuring data are then provided already before the catheter ablation is performed and can contribute to the later registration.

In the registration step 4 in the registration module 12, the dimensions of the 3D image data and of the 3D mapping data are also matched apart from the correlation in the correct position. This is required in order to achieve the most accurate superimposition possible of the 3D image data of the heart chamber or of its surface in the same position, orientation, scaling and shape with the corresponding visualization of the heart chamber from the 3D mapping data.

As a rule, this requires a transformation of the 3D image data or of the 3D mapping data which can include three degrees of freedom of translation, three degrees of freedom of rotation, three degrees of freedom of scaling and/or a number of vectors for the deformation.

In a first embodiment, the registration can take place by visual matching. For this purpose, an operator changes the data visualized until the position, orientation, scaling and/or shape of the heart chamber displayed matches in both representations, i.e. on the basis of the 3D image data and on the basis of the 3D mapping data. The visual matching can take place via a suitable graphical user interface 9.

Furthermore, artificial markers can be used for the registration. In one embodiment, the artificial markers can thus be attached to the chest of the patient before recording the 3D image data. These markers remain fixed at the same position during the entire subsequent catheter application. At least three of these markers are required for achieving correct registration, i.e. correlation of the image data with the mapping data. During this process, markers must be used which are both recognizable in the 3D image data and identifiable by the position sensor of the mapping system.

A further embodiment for registration provides the use of global anatomic markers, i.e. distinct natural points of the area to be treated or its environment, for a registration. These distinct points must be identifiable in the 3D image data and are preferably approached with the mapping catheter by using a fluoroscopic imaging technique. Such distinct points are, for example, the openings of the vena cava superior and inferior or of the coronary sinus. The distinct points can then be detected automatically in the 3D image data and the 3D mapping data so that a correlation of these data with the correct position and dimension can be calculated.

In addition, a registration between the position of the mapping catheter and of the 3D image data can also be carried out via such markers or distinct points. This registration makes it possible to visualize the position of the mapping catheter within the 3D image data.

A further advantageous possibility for the registration of the 3D image data and of the 3D mapping data resides in the automatic matching of the surfaces represented on the basis of these data. After the segmentation of the heart chamber to be treated, the extracted 3D surface contour of the heart chamber can be automatically matched to the surface contour of the heart chamber obtained by the 3D mapping data. In the case of deviations in the shape of the surface contours obtained from the 3D image data and the 3D mapping data, deforming matching algorithms can be applied to the surface contour from the 3D image data or to the surface contour from the 3D mapping data in order to improve the mutual mapping.

The surface matching can be performed, for example, by reducing or even minimizing point spaces between surface points of the mapping data and surface points of the 3D surface contour extracted from the 3D image data (point-to-point matching). As an alternative, the matching can also be performed by reducing or even minimizing point spaces between surface points of the mapping data and interpolated matching points of the 3D image data (point-to-surface matching).

The surface matching requires a good surface representation by the 3D mapping data of the heart chamber to be treated. However, since these data are collected over a relatively long period of time, as a rule, i.e. only few electroanatomical 3D mapping data are available at the beginning of the catheter ablation, a multi-stage process of the registration is preferably performed. In this process, a registration by a marker takes place in an initial first stage. The accuracy of the registration is then improved in the course of the process by surface matching in a second step.

Naturally, further steps of surface matching, by which a further increase in accuracy is possibly provided, can also be performed with the increasing number of mapping points. This multi-stage registration is of advantage since registration by surface matching, with a correspondingly good surface representation, is more accurate than registration by means of anatomical distinct points or artificial markers, but a good surface representation is only obtained in a later course of the method by the mapping data.

In the initial first stage, a combination of a registration by way of markers and of a registration by way of surface matching can also be effected. Thus, for example, a registration of the left atrium by surface matching of a vessel surface, e.g. of the pulmonary artery, and additionally by way of distinct anatomical points of the right atrium, e.g. of the coronary sinus or of the opening of the vena cava inferior or of the vena cava superior, can be effected.

A further possibility for the registration by way of surface matching consists in not using for the matching the surface of the chamber to be treated but the surface of another chamber which has already been electroanatomically measured before the beginning of the catheter application. This can be, for example, the right atrium which has been measured before a pulmonary vein isolation (PVI) of the left atrium. Naturally, measuring should take place with a sufficient number of surface points in this case. The resultant matching parameters for this chamber can then be applied to the data obtained during the catheter ablation.

In the preceding example embodiments, the surface matching was implemented as point-to-point or point-to-surface matching. Since the procedure of catheter ablation is performed on certain relatively small areas of the chamber to be treated, surface matching in these areas of interest provides more accurate results than in other areas of the chamber to be treated, due to the high density of mapping points. Higher weighting of surface points located within the area of interest, for example around the pulmonary veins in the case of a PVI, achieves better spatial matching in this area than in other areas of the heart chamber. The area of interest can be specified, for example, by a corresponding input by the operator at a graphical user interface.

Apart from this anatomic area of interest, surface points in the immediate vicinity of the moving catheter or its known position can be used for performing local surface matching. The higher weighting of these points results in better local matching around the catheter point than in other areas of the chamber to be treated. However, this method requires real-time registration during the catheter application in order to be able to continuously update the surface matching during the movement of the catheter.

After the registration between the 3D mapping data and the 3D image data, the superimposition with the correct position and dimension for visualizing the superimposed data is performed in step 5 in the visualization module 13. The dashed arrow in the FIGURE indicates the possibility of refining the registration or superimposition during the catheter ablation by way of a multi-stage process as has already been explained above.

For the superimposed visualization, which can take place, for example, on a monitor 6, different techniques can be used. Thus, in one embodiment, the visualization of the 3D image data or of the heart chamber to be treated, respectively, can be effected by means of a volume rendering technique (VRT). On the image data visualized by way of the volume rendering technique, the complete 3D mapping data can be superimposed which both show electrical activity and the instantaneous position of the catheter with spatial resolution. The transparency of both part-images, i.e. the part-image from the 3D image data and the part-image from the 3D mapping data, like the blending factor of the superimposition, can be changed by an operator in order to obtain suitable visualizations of the anatomy, the electrophysiology or simultaneously of both characteristics. Since the visualization of the 3D mapping data contains the visualization of the position and orientation of the mapping catheter, it is also possible only to superimpose the representation of the position and orientation of the mapping catheter on the 3D image data from time to time.

In a further embodiment, the surface extracted from the 3D image data can also be visualized as surface-shaded representation or, after triangulation, as polygonal grid. The polygonal grid is displayed together with the 3D mapping data in order to be able to visualize simultaneously the anatomy represented by the polygonal grid and the electrophysiology represented by the 3D mapping data. In this case, too, it is possible only to display the position and orientation of the mapping catheter together with the polygonal grid representing the surface, from time to time.

In a further embodiment, an endoscopic perspective can also be calculated from the recorded data and visualized by superimposing the anatomical 3D image data and electrophysiological 3D mapping data. By way of this endoscopic perspective, from the point of view of the tip of the catheter, the catheter can also be guided by the operator to the corresponding anatomical or electrophysiological positions, for example the opening of the pulmonary vein.

Furthermore, the recorded data can also be used for visualizing the distance of the catheter point from predeterminable areas. Since during the registration between the 3D mapping data and 3D image data, or during the registration between the position of the mapping catheter and the 3D image data, a spatial relation is obtained between the mapping catheter and the 3D image data, the distance of the tip of the catheter from predeterminable picture elements of the 3D image can be calculated at any time. This registration makes it possible to display the mapping catheter within the representation of the 3D image data—even without displaying the electrophysiological data, and at the same time to specify the distance.

Thus, for example, the distance of the catheter point from the target tissue can be visualized in real time in the representation. The visualization can take place, for example, by color representation of the catheter with color coding of the distance. This possibility of catheter representation can be used for planning and controlling ablation processes. Furthermore, due to the registration between the mapping catheter and the 3D image data, it is also possible to store the position of removed locations together with the image data. The position stored can be processed for documentation purposes and for the planning and control of subsequent ablation processes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method of visually supporting an electrophysiology catheter application in the heart, comprising:
   recording 3D image data of the area to be treated using a tomographical 3D imaging device before the catheter application;
   segmenting the 3D image data to extract a 3D surface profile of objects in an area to be treated from the 3D image data by segmentation; and
   correlating electroanatomical 3D mapping data and 3D image data representing the 3D surface profile by surface matching, in at least one stage of registration, the 3D surface profile from the 3D image data to a 3D surface profile from the 3D mapping data;
   displaying the correlated electroanatomical 3D mapping data and 3D image data representing at least the 3D surface profile, the displayed electroanatomical 3D mapping data and 3D image data representing at least the registered 3D surface profile with correct position and dimension, wherein,
      the at least one stage of registration includes a first stage of the performance of the catheter application and a later, second stage of the performance of the catheter application,
      the correlating in the first stage includes registering using the electroanatomical 3D mapping data captured during the first stage, and
      the correlating in the second stage includes registering using the registration obtained in the first stage and the electroanatomical 3D mapping data captured during the second stage,
      the first stage uses at least one of distinct anatomical points and artificial markers and the second stage refines the registration obtained in the first stage by the surface matching, and
   the displaying includes,
      displaying at least a part of a catheter in real time in the representation of the 3D image data representing at least the 3D surface profile,
      calculating an instantaneous distance of a tip of the catheter from a picture element of the 3D image data, and
      indicating the calculated distance by color coding the catheter.

2. The method as claimed in claim 1, wherein the recording records the 3D image data of the area to be treated with a method of at least one of X-ray computer tomography and magnetic resonance tomography.

3. The method as claimed in claim 1, wherein the recording records the 3D image data of the area to be treated using a 3D ultrasonic method.

4. The method as claimed in claim 1, wherein the displaying displays 3D image data via a volume rendering technique.

5. The method as claimed in claim 1, wherein display displays the 3D surface profile from the 3D image data as a polygonal grid.

6. The method as claimed in claim 1, wherein the displaying includes adjusting a transparency and adjusting a blending factor.

7. The method as claimed in claim 1, wherein the at least one part of the catheter is displayed without superimposition of the 3D mapping data from time to time.

8. A device, comprising:
   at least one input interface for electroanatomical 3D mapping data and 3D image data;
   a segmentation module configured to segment the 3D image data to extract a 3D surface profile of objects contained within a volume recorded using the 3D image data;
   a registration module connected to the segmentation module, the registration module configured to automatically correlate the electroanatomical 3D mapping data and the 3D image data representing the 3D surface profile by surface matching of the 3D surface profile from the 3D image data to a 3D surface profile from the 3D mapping data in at least one stage of the registration, the registration being carried out with correct position and dimension; and
   a display module connected to the registration module, the display module configured to display the correlated 3D mapping data and at least the 3D image data representing the 3D surface profile on one another in the correct position with the correct dimension, wherein,
      the at least one stage of registration includes a first stage of the performance of the catheter application and a later, second stage of the performance of the catheter application,
      the registration module is configured to,
         correlate in the first stage includes by registering using the electroanatomical 3D mapping data captured during the first stage, and
         correlate in the second stage includes by registering using the registration obtained in the first stage and the electroanatomical 3D mapping data captured during the second stage, the first stage uses at least one of distinct anatomical points and artificial markers and the second stage refines the registration obtained in the first stage by the surface matching, and the display module is configured to, display at least a part of a catheter in real time in the representation of the 3D image data representing at least the 3D surface profile, calculate an instantaneous distance of a tip of the catheter from a picture element of the 3D image data, and indicate the calculated distance by color coding the catheter.

9. A method of visually supporting an electrophysiology catheter application in the heart, comprising:

recording 3D image data of an area of the heart to be treated with a method of tomographical 3D imaging, before electroanatomical 3D mapping data is provided during the performance of the catheter application;

extracting a 3D surface profile of objects in the area to be treated from the 3D image data by segmentation;

registering, with correct position and dimension, by automatically correlating the electroanatomical 3D mapping data and 3D image data representing the 3D surface profile by surface matching, in at least one stage of registration, the 3D surface profile from the 3D image data to a 3D surface profile from the 3D mapping data; and displaying 3D mapping data and the 3D image data representing the 3D surface profile superimposed on one another in correct dimension and position, wherein, the at least one stage of registration includes a first stage of the performance of the catheter application and a later, second stage of the performance of the catheter application, the correlating in the first stage includes registering using the electroanatomical 3D mapping data captured during the first stage, the correlating in the second stage includes registering using the registration obtained in the first stage and the electroanatomical 3D mapping data captured during the second stage, the first stage uses at least one of distinct anatomical points and artificial markers and the second stage refines the registration obtained in the first stage by the surface matching, and the displaying includes, displaying at least a part of a catheter in real time in the representation of the 3D image data representing at least the 3D surface profile, calculating an instantaneous distance of a tip of the catheter from a picture element of the 3D image data, and indicating the calculated distance by color coding the catheter.

10. The method as claimed in claim 9, wherein the recording records the 3D image data of the area to be treated with a method of at least one of X-ray computer tomography and magnetic resonance tomography.

11. The method as claimed in claim 9, wherein the recording records the 3D image data of the area to be treated using a 3D ultrasonic method.

12. A device for visually supporting an electrophysiology catheter application in the heart, comprising:

means for recording 3D image data of an area of the heart to be treated with a method of tomographical 3D imaging, before electroanatomical 3D mapping data is provided during the performance of the catheter application;

means for extracting a 3D surface profile of objects in the area to be treated from the 3D image data by segmentation;

means for correlating electroanatomical 3D mapping data and 3D image data representing the 3D surface profile by surface matching, in at least one stage of registration, the 3D surface profile from the 3D image data to a 3D surface profile from the 3D mapping data;

means for displaying the correlated electroanatomical 3D mapping data and 3D image data representing at least the 3D surface profile superimposed on one another, with correct position and dimension, wherein, the at least one stage of registration includes a first stage of the performance of the catheter application and a later, second stage of the performance of the catheter application, the means for correlating correlates in the first stage using the electroanatomical 3D mapping data captured during the first stage, and the means for correlating correlates in the second stage using the registration obtained in the first stage and the electroanatomical 3D mapping data captured during the second stage, the first stage uses at least one of distinct anatomical points and artificial markers and the second stage refines the registration obtained in the first stage by the surface matching, the means for displaying displays at least a part of a catheter in real time in the representation of the 3D image data representing at least the 3D surface profile, the means for displaying calculates an instantaneous distance of a tip of the catheter from a picture element of the 3D image data, and the means for displaying indicates the calculated distance by color coding the catheter.

13. The device as claimed in claim 12, wherein the means for recording records the 3D image data of the area to be treated with at least one of X-ray computer tomography and magnetic resonance tomography.

14. The device as claimed in claim 12, wherein the means for recording records the 3D image data of the area to be treated using 3D ultrasound.

* * * * *